United States Patent
Barger et al.

[11] Patent Number: 5,990,369
[45] Date of Patent: Nov. 23, 1999

[54] PROCESS FOR PRODUCING LIGHT OLEFINS

[75] Inventors: Paul T. Barger; R. Joe Lawson, both of Arlington Heights; Bipin V. Vora, Darien, all of Ill.

[73] Assignee: UOP LLC, Des Plaines, Ill.

[21] Appl. No.: 09/021,044

[22] Filed: Feb. 9, 1998

Related U.S. Application Data

[63] Continuation-in-part of application No. 08/513,371, Aug. 10, 1995, abandoned.

[51] Int. Cl.$^6$ ............................... C07C 1/20; C07C 2/00; C07C 5/23

[52] U.S. Cl. ......................... 585/640; 585/314; 585/315; 585/324; 585/664; 585/638; 585/639; 585/643; 585/644; 585/645; 585/646; 585/647

[58] Field of Search ...................................... 585/638, 639, 585/640, 643, 644, 645, 646, 647, 314, 315, 324, 664

[56] References Cited

U.S. PATENT DOCUMENTS

| | | | |
|---|---|---|---|
| 3,723,562 | 3/1973 | Heckelsberg . | |
| 3,928,483 | 12/1975 | Chang et al. . | |
| 4,025,575 | 5/1977 | Chang et al. . | |
| 4,052,479 | 10/1977 | Chang et al. . | |
| 4,252,479 | 2/1981 | Scherfenberg . | |
| 4,447,669 | 5/1984 | Hamon et al. | 585/640 |
| 4,496,786 | 1/1985 | Santilli et al. | 585/640 |
| 4,499,314 | 2/1985 | Seddon et al. | 585/408 |
| 4,547,616 | 10/1985 | Avidan et al. | 585/640 |
| 4,590,174 | 5/1986 | Kukes et al. | 502/219 |
| 4,677,242 | 6/1987 | Kaiser | 585/638 |
| 4,677,243 | 6/1987 | Kaiser | 585/638 |
| 4,843,183 | 6/1989 | Inui | 585/640 |
| 4,861,938 | 8/1989 | Lewis et al. | 585/640 |
| 4,973,792 | 11/1990 | Lewis et al. | 585/638 |
| 5,026,935 | 6/1991 | Leyshon et al. | 585/315 |
| 5,026,936 | 6/1991 | Leyshon et al. | 585/315 |
| 5,095,163 | 3/1992 | Barger | 585/640 |
| 5,126,308 | 6/1992 | Barger et al. | 502/214 |
| 5,132,484 | 7/1992 | Gajda | 585/667 |
| 5,191,141 | 3/1993 | Barger et al. | 585/640 |

FOREIGN PATENT DOCUMENTS

| | | |
|---|---|---|
| 0129900B1 | 1/1989 | European Pat. Off. . |
| WO93/13013 | 7/1993 | WIPO . |

OTHER PUBLICATIONS

Peters et al., Plant Design and Economics For Chemical Engineers, Third Edition, pp. 6–7 No month vailable, 1980.

Inui, T., "Structure–Reactivity Relationships in Methanol to Olefin Conversion on Various Microporous Crystalline Catalysts," Grasseli, R.K. and Sleight A.W., Eds. of *Structure–Activity and Selectivity Relationships in Heterogeneous Catalysis*, (Amsterdam, Elsevier Science Publishers B.V., 1991) pp. 233–242. no month available.

*Primary Examiner*—Elizabeth D Wood
*Attorney, Agent, or Firm*—Thomas K. McBride; John G. Tolomei; Richard P. Silverman

[57] ABSTRACT

The present invention relates to a process for the production of light olefins comprising olefins having from 2 to 4 carbon atoms per molecule from an oxygenate feedstock. The process comprises passing the oxygenate feedstock to an oxygenate conversion zone containing a metal alumninophosphate catalyst to produce a light olefin stream. The light olefin stream is fractionated and a portion of the products are metathesized to enhance the yield of the ethylene, propylene, and/or butylene products. Propylene can be metathesized to produce more ethylene, or a combination of ethylene and butene can be metathesized to produce more propylene. This combination of light olefin production and metathesis, or disproportionation provides flexibility to overcome the equilibrium limitations of the metal aluminophosphate catalyst in the oxygenate conversion zone. In addition, the invention provides the advantage of extended catalyst life and greater catalyst stability in the oxygenate conversion zone.

16 Claims, 3 Drawing Sheets

PROCESS FOR PRODUCING LIGHT OLEFINS

CROSS-REFERENCE TO RELATED APPLICATIONS

This application is a continuation-in-part of U.S. application Ser. No. 08/513,371, filed Aug. 10, 1995, now abandoned, and is hereby incorporated by reference.

FIELD OF THE INVENTION

This invention relates to a process for the production of light olefins from an oxygenate feedstream.

BACKGROUND OF THE INVENTION

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of the Third World strain toward growth and expansion, the demand for light olefins will increase dramatically.

The search for alternative materials for light olefin production has led to the use of oxygenates such as alcohols, and more particularly to the use of methanol, ethanol, and higher alcohols or their derivatives. These alcohols may be produced by fermentation or from synthesis gas. Synthesis gas can be produced from natural gas, petroleum liquids, and carbonaceous materials including coal, recycled plastics, municipal wastes, or any organic material. Thus, alcohol and alcohol derivatives may provide non-petroleum based routes for the production of olefin and other related hydrocarbons.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483, 4,025,575, 4,252,479 (Chang et al.); U.S. Pat. No. 4,496,786 (Santilli et al.); U.S. Pat. No. 4,547,616 (Avidan et al.); U.S. Pat. No. 4,677,243 (Kaiser); U.S. Pat. No. 4,843,183 (Inui); U.S. Pat. No. 4,499,314 (Seddon et al.); U.S. Pat. No. 4,447,669 (Harmon et al.); U.S. Pat. No. 5,095,163 (Barger); U.S. Pat. No. 5,191,141 (Barger); U.S. Pat. No. 5,126,308 (Barger); U.S. Pat. No. 4,973,792 (Lewis); and U.S. Pat. No. 4,861,938 (Lewis).

The process may be generally conducted in the presence of one or more diluents which may be present in the oxygenate feed in an amount between about 1 and about 99 molar percent, based on the total number of moles of all feed and diluent components fed to the reaction zone (or catalyst). Diluents include—but are not limited to—helium, argon, nitrogen, carbon monoxide, carbon dioxide, hydrogen, water, paraffins, hydrocarbons (such as methane and the like), aromatic compounds, or mixtures thereof. U.S. Pat. Nos. 4,861,938 and 4,677,242 particularly emphasize the use of a diluent combined with the feed to the reaction zone to maintain sufficient catalyst selectivity toward the production of light olefin products, particularly ethylene. The above U.S. Patents are hereby incorporated by reference.

U.S. Pat. No. 5,026,935 to Leyshon et al. discloses a process for the preparation of ethylene from $C_4$ or higher feed by the combination of cracking and metathesis to form ethylene and propylene and at least a portion of the propylene is metathesized to ethylene. U.S. Pat. No. 4,590,174 to Kukes et al. discloses an olefin metathesis process employing a catalyst comprising an inorganic refractory oxide support containing at least one of tungsten oxide and molybdenum oxide and a promoting agent for the disproportionation reaction. Example 3 of U.S. Pat. No. 3,723,562 describes the conversion of propylene to a mixture of ethylene and butenes using a $WO_3$—$SiO_2$ catalyst containing about 8 weight per cent tungsten oxide. Conditions used were 800° F., 100 psig and 15 $hr^{-1}$ WHSV. Propylene conversion was 19% with 37.6% selectivity to ethylene and 62.4% selectivity to butenes. U.S. Pat. No. 3,723,562 is hereby incorporated by reference.

European Publication No. 129900A to Wagner et al. discloses a process for the production of 1-butene from $C_4$ hydrocarbon mixtures containing 2-butene. The $C_4$ hydrocarbon mixture is isomerized in a reaction zone to 1-butene in the presence of an acid catalyst. The isomerization zone effluent is distilled to recover a hydrogen offgas, a 1-butene side-draw product, and 2-butene in a bottom stream. The bottom stream is recycled to the isomerization zone for the further isomerization of the 2-butene to 1-butene. The process is operated in the absence of steam without significant cracking or skeletal isomerization.

International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefin (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air. In a paper by T. Inui, titled, "Structure-Reactivity Relationships in Methanol to Olefins Conversion on Various Microporous Crystalline Catalysts," which was included in *STRUCTURE-ACTIVITY AND SELECTIVITY RELATIONSHIPS IN HETEROGENEOUS CATALYSIS*, edited by R. K. Grasselli and A. W. Sleight, Elsevier Science Publishers B.V., Amsterdam, 1991, on pages 233–242, Inui discloses the highest reported ratio of ethylene/propylene produced from methanol over a SAPO-34 catalyst as about 15:1 (See FIG. 4, page 240).

Generally the ratio of ethylene/propylene on a carbon basis varies from about 0.1 to about 10 and more typically varies from about 0.8 to about 2.5. This narrow band limits the flexibility of the process and the value of the net products produced. Methods are sought to alter the product distribution of the MTO process for making light olefins to provide processing flexibility and overcome the equilibrium limitations of the aluminophosphate catalyst of the MTO process. These and other disadvantages of the prior art are overcome by the present invention, and a new improved process for conversion of oxygenates to hydrocarbons is provided.

SUMMARY OF THE INVENTION

In the present invention, a combination of a light olefin production, or oxygenate conversion process step and an olefin metathesis process is employed to improve the amount of desirable olefin products beyond the equilibrium amount provided by a molecular sieve catalyst. By the process of the present invention, the yield ratio of ethylene to propylene is significantly improved and significant catalyst life and operating cost savings are obtainable. In one embodiment, the propylene yields can be reduced in favor of the more profitable and desirable ethylene and butylene products and the catalyst life and stability of aluminophosphate, or silicoaluminophosphate (SAPO) catalyst in the oxygenate conversion zone can be improved. Preferably the ratio of ethylene to propylene from a combination of oxygenation conversion and metathesis is between about 0.1 and about 1000, and more preferably, the ratio of ethylene to propylene for the combination is between about 0.8 and about 100, and most preferably, the ratio of ethylene to propylene for the combination is between about 0.8 and about 20. In another embodiment, the olefin metathesis reaction step is employed to convert a light olefin stream comprising ethylene and butylene into additional amounts of propylene. In either embodiment, a separation step such as fractionation to separate the light olefin stream into its individual components is required prior to selectively reacting the components separately or in any combination in the olefin metathesis reaction zone. When the light olefin stream introduced to the metathesis reaction zone comprises a ratio of ethylene to butylene ranging from about 0.5 to about 5.0, the ratio of the primary ethylene product stream to the secondary light olefin product stream, comprising propylene ranges from about 0.5 to about 2.

In one embodiment, the invention provides a process for the production of a primary light olefin product stream and a secondary olefin product stream from an aliphatic hetero compound feedstock. The process comprises the steps of reacting the aliphatic hetero compound feedstock in the presence of a molecular sieve catalyst, and more particularly an aluminophosphate catalyst, to produce a reactor effluent stream comprising ethylene, propylene, and butylene. The reactor effluent stream and a metathesized stream are fractionated to recover a propylene stream, an ethylene stream, and a butylene stream. At least a portion of a light olefin stream selected from the group consisting of the ethylene stream, the propylene stream, the butylene stream and mixtures thereof is metathesized to provide the metathesized stream which comprises ethylene, propylene, and butylene. The metathesized stream is returned to the fractionating step. The ethylene stream is withdrawn as the primary ethylene product stream and a secondary light olefin product stream selected from the group consisting of the propylene stream, the butylene stream and mixtures thereof is withdrawn from the process.

In another embodiment, the invention comprises a process for the production of a primary ethylene product stream and a secondary light olefin product stream. The secondary light olefin product stream comprises propylene. The process comprises the steps of reacting a feedstock comprising methanol or dimethyl ether in the presence of a diluent at effective conditions over a SAPO catalyst selected from a group consisting of SAPO-34, SAPO-17 and mixtures thereof to produce a reactor effluent stream comprising ethylene, propylene, and butylene. The reactor effluent stream and a metathesized stream are fractionated in a fractionating step to recover an ethylene stream, a propylene stream, and a butylene stream. At least a portion of the ethylene stream and a portion of the butylene stream are metathesized in a metathesis zone at effective conditions to produce the metathesized stream comprising ethylene, propylene, and butylene. The metathesized stream is returned to the fractionating step and the ethylene stream is withdrawn as the primary ethylene product stream. The propylene stream is withdrawn as the secondary light olefin product stream.

In a further embodiment, the invention is a process for the production of a primary ethylene product stream and a secondary light olefin product stream comprising butylene from a feedstock comprising methanol or dimethyl ether. The process comprises the steps of reacting the feedstock in the presence of a diluent at effective conditions over a SAPO catalyst selected from the group consisting of SAPO-34, SAPO-17, and mixtures thereof to produce a reactor effluent stream comprising ethylene, propylene, and butylene. The reactor effluent stream is fractionated in a fractionating step along with a metathesized stream to recover an ethylene stream, a propylene stream, and a butylene stream. At least a portion of the propylene stream is metathesized in a metathesis zone at effective conditions to produce the metathesized stream comprising ethylene and butylene. The metathesized stream is returned to the fractionating step and the ethylene stream is withdrawn as the primary ethylene product stream and the butylene stream is withdrawn as the secondary light olefin product stream.

DETAILED DESCRIPTION OF THE INVENTION

This invention comprises a process for the catalytic conversion of a feedstock comprising one or more aliphatic hetero compounds comprising alcohols, halides, mercaptans, sulfides, amines, ethers, and carbonyl compounds or mixtures thereof to a hydrocarbon product containing light olefinic products, i.e., $C_2$, $C_3$ and/or $C_4$ olefins. The feedstock is contacted with a silicoaluminophosphate molecular sieve at effective process conditions to produce light olefins. Silicoaluminophosphate (SAPO) molecular sieves which produce light olefins are generally employable in the instant process. The preferred silicoaluminophosphates are those described in U.S. Pat. No. 4,440,871. Silicoaluminophosphate molecular sieves employable in the instant process are more fully described hereinafter.

The instant process employs a feedstock comprising "aliphatic hetero compounds." The term "aliphatic hetero compounds" is employed herein to include alcohols, halides, mercaptans, sulfides, amines, ethers and carbonyl compounds (aldehydes, ketones, carboxylic acids and the like). The aliphatic moiety preferably contains from 1 to about 10 carbon atoms and more preferably contains from 1 to about 4 carbon atoms. Suitable reactants include lower straight or branched chain alkanols, their unsaturated counterparts, and the nitrogen, halogen and sulfur analogue of such. Representative of suitable aliphatic hetero compounds include: methanol; methyl mercaptan; methyl sulfide; methyl amine; dimethyl ether; ethanol; ethyl mercaptan; ethyl chloride; diethyl ether; methyethyl ether; formaldehyde; dimethyl ketone; acetic acid; n-alkyl amines; n-alkyl halides and n-alkyl sulfides having n-alkyl group having 3 to 10 carbon atoms; and mixtures thereof.

In accordance with the process of the present invention, an aliphatic hetero compound feedstock is catalytically converted to hydrocarbons containing aliphatic moieties such as—but not limited to—methane, ethane, ethylene, propane, propylene, butylene, and limited amounts of other higher aliphatics by contacting the aliphatic hetero compound feedstock with a preselected catalyst. The term "aliphatic compound feedstock" as employed in the present invention and described herein designates only the organic material used as the feed. The total charge of feed to the aliphatic conversion reaction zone may contain additional compounds such as diluents. The term "oxygenate"—as employed in the present invention and described herein—designates compounds such as alcohols, ethers, aldehydes, ketones, and mixtures thereof. The invention will be herein discussed further with reference to oxygenates and an oxygenate conversion process which are the more preferred embodiments of the invention.

A diluent is required to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons, (e.g., methane), aromatic hydrocarbons, (e.g., benzene, toluene), and mixtures thereof. The amount of diluent used can vary considerably and is usually from about 5 to about 90 mole percent of the feedstock and preferably from about 25 to about 75 mole percent. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to about 0.1–5 moles of water have been disclosed.

The oxygenate conversion step of the present invention is preferably conducted in the vapor phase such that the oxygenate feedstock is contacted in a vapor phase in a reaction zone with a molecular sieve catalyst at effective process conditions to produce hydrocarbons, i.e., an effective temperature, pressure, weight hourly space velocity (WHSV) and, optionally, an effective amount of diluent, correlated to produce hydrocarbons. The process is affected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected. The oxygenate feedstock flow rate affects olefin production. Increasing the feedstock flow rate increases WHSV and enhances the formation of olefin production relative to paraffin production. However, the enhanced olefin production relative to paraffin production is offset by a diminished conversion of oxygenate to hydrocarbons.

The oxygenate conversion process is effectively carried out over a wide range of pressures, including autogenous pressures. At pressures between about 0.001 atmospheres (0.1 kPa) and about 1000 atmospheres (101.3 MPa), the formation of light olefin products will be affected although the optimum amount of product will not necessarily form at all pressures. The preferred pressure is between about 0.01 atmospheres (0.1 kPa) and about 100 atmospheres (10.13 MPa). More preferably, the pressure will range from about 1 to about 10 atmospheres(101.3 kPa to 1.013 MPa). The pressures referred to herein for the process are exclusive of the inert diluent, if any, that is present and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range and beyond, the selectivities, conversions and/or rates to light olefin products may not occur at the optimum, although light olefin such as ethylene may still be formed.

The temperature which may be employed in the oxygenate conversion process may vary over a wide range depending, at least in part, on the selected molecular sieve catalyst. In general, the process can be conducted at an effective temperature between about 200° C. (392° F.) and about 700° C. (1292° F.). Temperatures outside the stated range are not excluded, although they do not fall within certain desirable embodiments of the present invention. At the lower end of the temperature range, and thus, generally at a lower rate of reaction, the formation of the desired light olefin products may become markedly slow. At the upper end of the temperature range and beyond, the process may not form an optimum amount of light olefin products and catalyst deactivation may be rapid. Notwithstanding these factors, the reaction will still occur and the feedstock, at least in part, can be converted to the desired light olefin products at temperatures outside the range between about 200° C. (392 ° F.) and about 700° C. (1292 ° F.).

The selection of a particular catalyst for use in the oxygenate conversion step depends upon the particular oxygenate conversion desired but in a preferred aspect of the present invention where the oxygenate feedstock is converted into light olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *ZEOLITE MOLECULAR SIEVES* by John Wiley & Sons, New York (1974), hereby incorporated by reference in its entirety. The term effective diameter is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves, and non-zeolitic molecular sieves.

Zeolitic molecular sieves in the calcined form may be represented by the general formula:

$$Me_{2/n}O:Al_2O_3:xSiO_2:yH_2O$$

where Me is a cation, x has a value from about 2 to infinity, n is the cation valence and y has a value of from about 2 to 10.

Typically, well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11, and MCM-22. Other zeolites include those having a high silica content, i.e., those having silica to alumina ratios greater than 10 and typically greater than 100 can also be used. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of elements, x represents the total amount of the metal mixture present. Preferred elements (EL) are silicon, magnesium and cobalt with silicon being especially preferred.

The preparation of various ELAPOs are well known in the art and may be found in U.S. Pat. No. 5,191,141 (ELAPO); U.S. Pat. No. 4,554,143 (FeAPO); U.S. Pat. No. 4,440,871 (SAPO); U.S. Pat. No. 4,853,197 (MAPO, MnAPO, ZnAPO, CoAPO); U.S. Pat. No. 4,793,984 (CAPO), U.S. Pat. Nos. 4,752,651 and 4,310,440 all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH). The reaction mixture is placed in a sealed pressure vessel, optionally lined with an inert plastic material such as polytetrafluoroethylene and heated preferably under autogenous pressure at a temperature between about 50° C. and 250° C. and preferably between about 100° C. and 200° C. for a time sufficient to produce crystals of the ELAPO molecular sieve. Typically the time varies from about 2 hours to about 720 hours and preferably from about 4 hours to about 440 hours. The desired product is recovered by any convenient method such as centrifugation or filtration. It is known that the particle size of the ELAPO molecular sieve can be reduced by stirring the reaction mixture at high speeds and by using TEAOH as the templating agent. It is preferred that the ELAPO molecular sieves are composed of particles at least 50% of which have a particle size less than 1.0 μm and no more than 10% of the ELAPO particles have a particle size greater than 2.0 μm.

The ELAPOs which are synthesized using the process described above will usually contain some of the organic templating agent in its pores. In order for the ELAPOs to be active catalyst, the templating agent in the pores must be removed by heating the ELAPO powder in an oxygen containing atmosphere at a temperature of about 200° C. to about 700° C. until the template is removed, usually a few hours. A preferred embodiment of the invention is one in which the element (EL) content varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The molecular sieve catalyst for the oxygenate conversion zone preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like. If matrix materials, e.g., binder and/or filler materials, are included in the catalyst composition, the non-zeolitic and/or zeolitic molecular sieves preferably comprise about 1 to 99%, more preferably about 5 to about 90% and still more preferably about 10 to about 80%, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material and returned to the oxygenate conversion reaction zone.

Depending upon the particular catalyst and conversion, it can be desirable to substantially remove the carbonaceous material e.g., to less than 1 wt %, or only partially regenerate the catalyst, e.g., to from about 2 to 30 wt % carbon. Preferably, the regenerated catalyst will contain about 0 to 20% and more preferably from about 0 to 10% carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration.

The metathesis or disproportion reaction is carried out under conditions and using catalysts which are known in the art. Generally, a metathesis catalyst containing a catalytic amount of at least one of molybdenum oxide and tungsten oxide is suitable for the metathesis reaction. Conditions of the metathesis generally include reaction temperature ranging from about 100° to about 450° C., preferably 150° to 350° C., and pressures varying from about atmospheric to upwards of 3,000 psig, although higher pressures can be employed if desired. Catalysts which are active for the metathesis of olefins and which can be used in the process of this invention are of a generally known type. In this regard, reference is made to "Journal of Molecular Catalysis", 28 (1984) pages 117–131, to "Journal of Catalysis", 13 (1969) pages 99–113, to "Applied Catalysis" 10 (1984) pages 29–229 and to "Catalysis Reviews", 3 (1) 1969) pages 37–60.

Such metathesis catalysts may be homogeneous or heterogeneous, with heterogeneous catalysts being preferred. The metathesis catalyst preferably comprises a catalytically effective amount of transition metal component. The preferred transition metals for use in the present invention include tungsten, molybdenum, nickel, rhenium, and mixtures thereof. The transition metal component may be present as elemental metal and/or one or more compounds of the metal. If the catalyst is heterogeneous, it is preferred that the transition metal component be associated with a support. Any suitable support material may be employed provided that it does not substantially interfere with the feedstock components or the lower olefin component conversion. Preferably, the support material is an oxide, such as silica, alumina, titania, zirconia and mixtures thereof. Silica is a particularly preferred support material. If a support material is employed, the amount of transition metal component used in combination with the support material may vary widely depending, for example, on the particular application involved and/or the transition metal being used. Preferably, the transition metal comprises about 1% to about 20%, by weight (calculated as elemental metal) of the total catalyst. The metathesis catalyst advantageously comprise a catalytically effective amount of at least one of the above-noted transition metals, and are capable of promoting olefin metathesis. The catalyst may also contain at least one activating agent present in an amount to improve the effectiveness of the catalyst. Various activating agents may be employed, including activating agents which are well known in the art to facilitate metathesis reactions.

The metathesis reactor effluent is resolved by conventional separation means into a product ethylene fraction, a propylene fraction which can be recycled, and a butene and higher hydrocarbon fraction.

The specified combination of the conversion of the feedstock to a mixture of light olefins at conditions favoring the production of these components coupled with the use of the thus formed propylene to produce further quantities of product ethylene provides a synergistic combination of oxygenate conversion and metathesis reaction steps whereby there are obtained substantially improved overall yields of the desired light olefins: ethylene and butylene. Preferably the ratio of ethylene to propylene ranges from about 0.1 to about 1000, and more preferably the ratio of ethylene to propylene ranges from about 0.8 to about 100, and most preferably the ratio of ethylene to propylene ranges from about 0.8 to about 20. When portions of the ethylene and butylene are introduced at effective conditions to the metathesis zone in a molar ratio of about 0.5 to about 5 ethylene to butylene, additional amounts of propylene are produced.

DETAILED DESCRIPTION OF THE DRAWINGS

The process of the present invention is hereinafter described with reference to the figures (FIG. 1, FIG. 2, and FIG. 3) which illustrate various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the figure may be modified in many aspects without departing from the basic overall concept of the invention.

Figure 1:
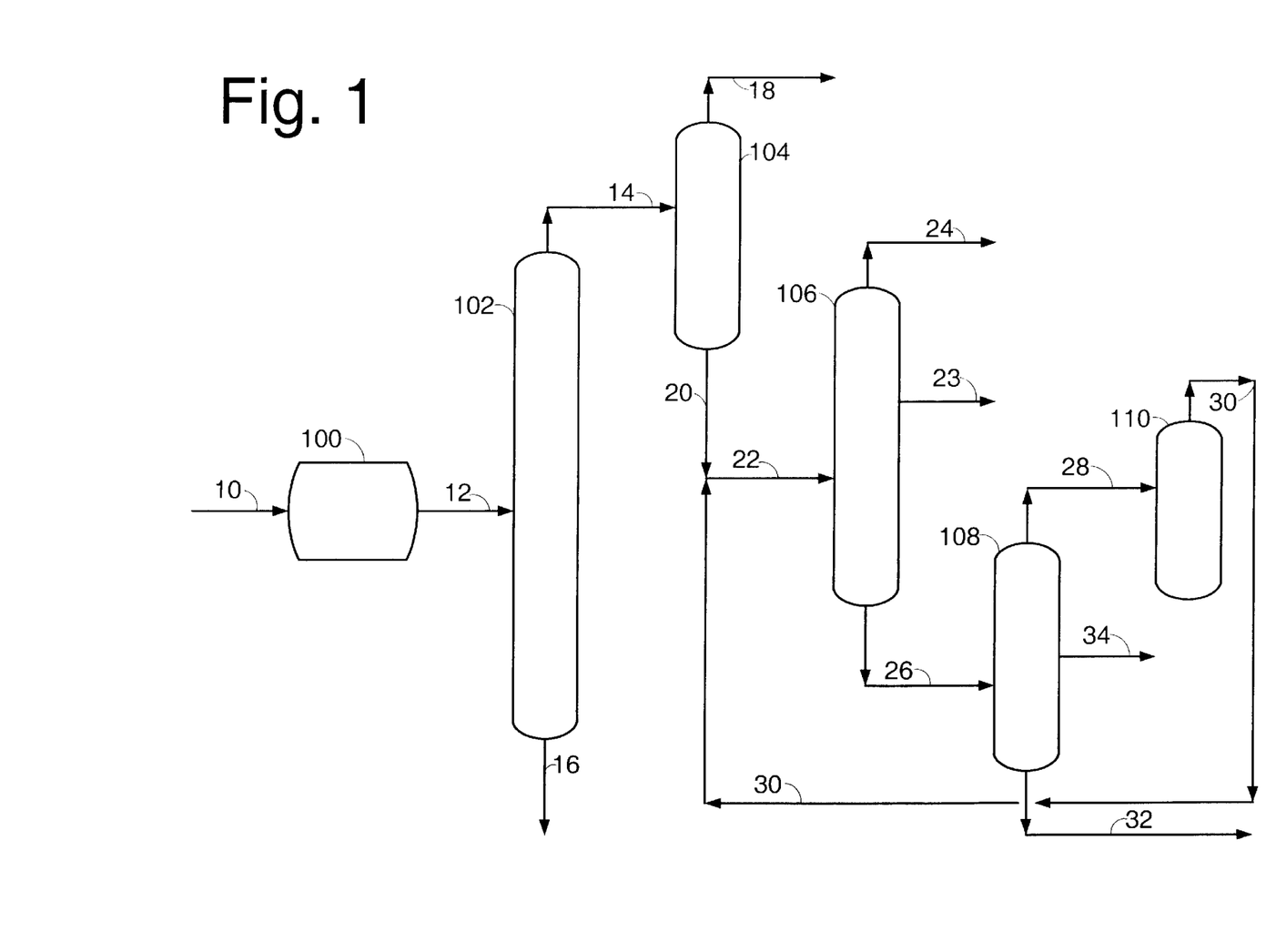
FIG. 1 is a schematic process flow diagram illustrating the process of the instant invention employing a metathesis, or disproportionation zone to enhance the yield of ethylene and butylene.

FIG. 1 is a schematic flowsheet of the process of the current invention. With reference to the Fig. a, a feedstream 10 comprising an oxygenate such as at least one of methanol, ethanol, propanol, or dimethyl ether is passed to an oxygenate conversion zone 100 wherein at least a portion of the feedstream is converted to light olefins in the presence of a diluent in a fluidized bed containing a metal aluminophosphate catalyst. The metal aluminophosphate catalyst is preferably a SAPO catalyst such as SAPO-34, SAPO-17 and mixtures thereof with a binder. A reactor effluent stream comprising light olefins, such as ethylene, propylene, and butylene is withdrawn in line 12 and passed to a water separation zone 102. In the water separation zone 102, the reactor effluent is flashed at a separation temperature which is lower than the reactor temperature to provide a vapor effluent stream 14 and a water stream 16. Although not shown in the FIG. 1, the vapor effluent stream 14 may be further conventionally washed with a caustic solution to neutralize any acid gases and remove catalyst fines and dried prior to passing the vapor effluent stream 14 to a demethanizer zone 104. In the demethanizer zone 104, the vapor effluent stream 14 is fractionated by conventional distillation methods to provide a light ends stream 18 comprising methane and a demethanized stream 20 comprising components heavier than methane, such as ethylene, propylene, and butylene. The demethanized stream 20 and a metathesized stream 30 are passed to a $C_2$ fractionation zone 106 via lines 20 and 22 and fractionated to provide a $C_3$ plus stream 26, an ethylene product stream 24 and an ethane stream 23. Depending upon the yield of ethylene and the amount of ethane present, the $C_2$ fractionation can take place in a single column or the $C_2$ fractionation zone may contain a deethanizer column to separate a $C_2$ stream from the $C_3$ plus stream 26 and an ethylene column to separate the $C_2$ stream into the ethylene product stream 24 and the ethane stream 23. The $C_3$ plus stream 26 is passed to a $C_3$ fractionation zone 108 to provide a propylene stream 28, a $C_4^+$ stream 32, and a propane stream 34. The $C_3$ fractionation zone 108 may consist of a single fractionator wherein the propane stream 34 is withdrawn as a sidedraw, or it may consist of a depropanizer column to first separate the $C_3$ plus stream 26 into a $C_3$ stream comprising propylene and propane and the $C_4^+$ stream 32, and a $C_3$ splitter column to fractionate the $C_3$ stream to provide the propylene stream 28 and the propane stream 34. The ethane and propane streams 23 and 34 may be used to provide fuel for the complex. At least a portion of propylene stream 28 is passed to a disproportionation zone 110 containing a metathesis catalyst at disproportionation conditions to metathesize at least a portion of propylene to ethylene and butylene and produce a second reactor effluent stream 30. At least a portion of the second reactor effluent stream, or metathesized stream, comprising ethylene and butylene is returned to the $C_2$ fractionation zone 106 via lines 30 and 22 to provide fractionation of the product of the disproportionation zone 110.

Figure 2:
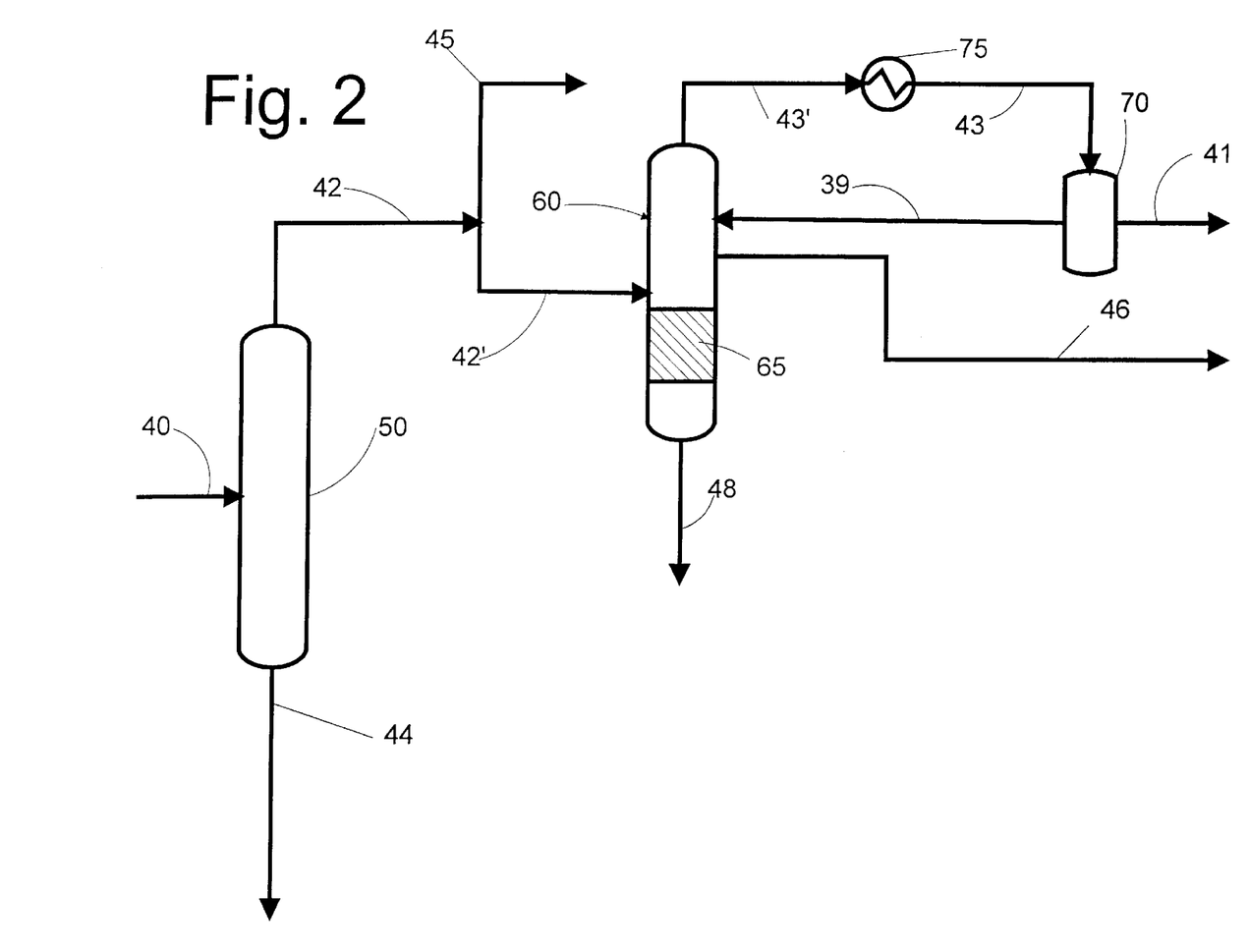
FIG. 2 is a schematic process flow diagram illustrating the conversion of the mixed butenes produced by the process of the present invention to form 1-butene by an isomerization reaction with distillation.

According to FIG. 2, the $C_4^+$ stream 32 can be further fractionated in a $C_4$ fractionation zone 50 to provide a mixed butylene product 42 and a heavier olefinic stream 44. A portion of the mixed butylene product 42 may be withdrawn as a finished product in line 45, or converted to other petrochemicals such as butene-1, or to gasoline blending components such as MTBE, and dimers such as octenes. As shown in FIG. 2, a portion of the mixed butylene product 42 comprising 1-butene and 2-butene is passed to a distillation with reaction zone 60 to isomerize the 2-butene to 1-butene over a suitable catalyst in an isomerization reaction zone 65 and recover a 1-butene product 46 and a small drag stream 48 comprising heavier olefins. A hydrogen offgas stream 41 is also produced. The overhead stream from the distillation zone 60 is passed via line 43' to a condenser 75 wherein the overhead is cooled to condense the $C_4$ hydrocarbons in the overhead stream producing a condensed stream 43 and the condensed stream 43 is passed to an accumulator 70. A portion of the condensed stream is returned to the distillation zone in line 39 to provide reflux to the distillation zone and the hydrogen offgas 41 produced during the isomerization reaction is withdrawn. The 1-butene product is withdrawn as a sidedraw in line 46. The 1-butene may be used with ethylene in manufacturing polymers such as linear low density polyethylene. The drag stream 48 may be used as fuel. A suitable catalyst for the isomerization of 2-butene to 1-butene is disclosed in U.S. Pat. No. 5,132,484. Although suitable acid catalyst may be employed, a non-zeolitic molecular sieve catalyst selected from the group consisting of SAPO-11, SAPO-31, SAPO-41 and mixtures thereof is preferred. More preferably, the butene isomerization catalyst comprises SAPO-11 as disclosed in U.S. Pat. No. 4,440,871, incorporated herein by reference. Most preferably, the butane isomerization catalyst comprises a SAPO-11 material which has been acid-washed in the conventional manner. The preferred operating conditions for the isomerization with reaction zone comprises a temperature ranging from about 50° C. to about 300° C., a pressure ranging from about 100 kPa to about 7 MPa, a LHSV (liquid hourly space velocity) ranging from about 0.2 to 10 $hr^{-1}$, and hydrogen to hydrocarbon molar ratio of from about 0.5 to 10. The mixed butene feed 42 is passed to the distillation zone 60 at a point above the isomerization zone 65. Heat of reaction produced in the isomerization zone is permitted to partially reboil the distillation zone 60. As an alternative, the isomerization with distillation may be arranged with a side reactor as disclosed in U.S. Pat. No. 5,395,981, hereby incorporated by reference.

Figure 3:
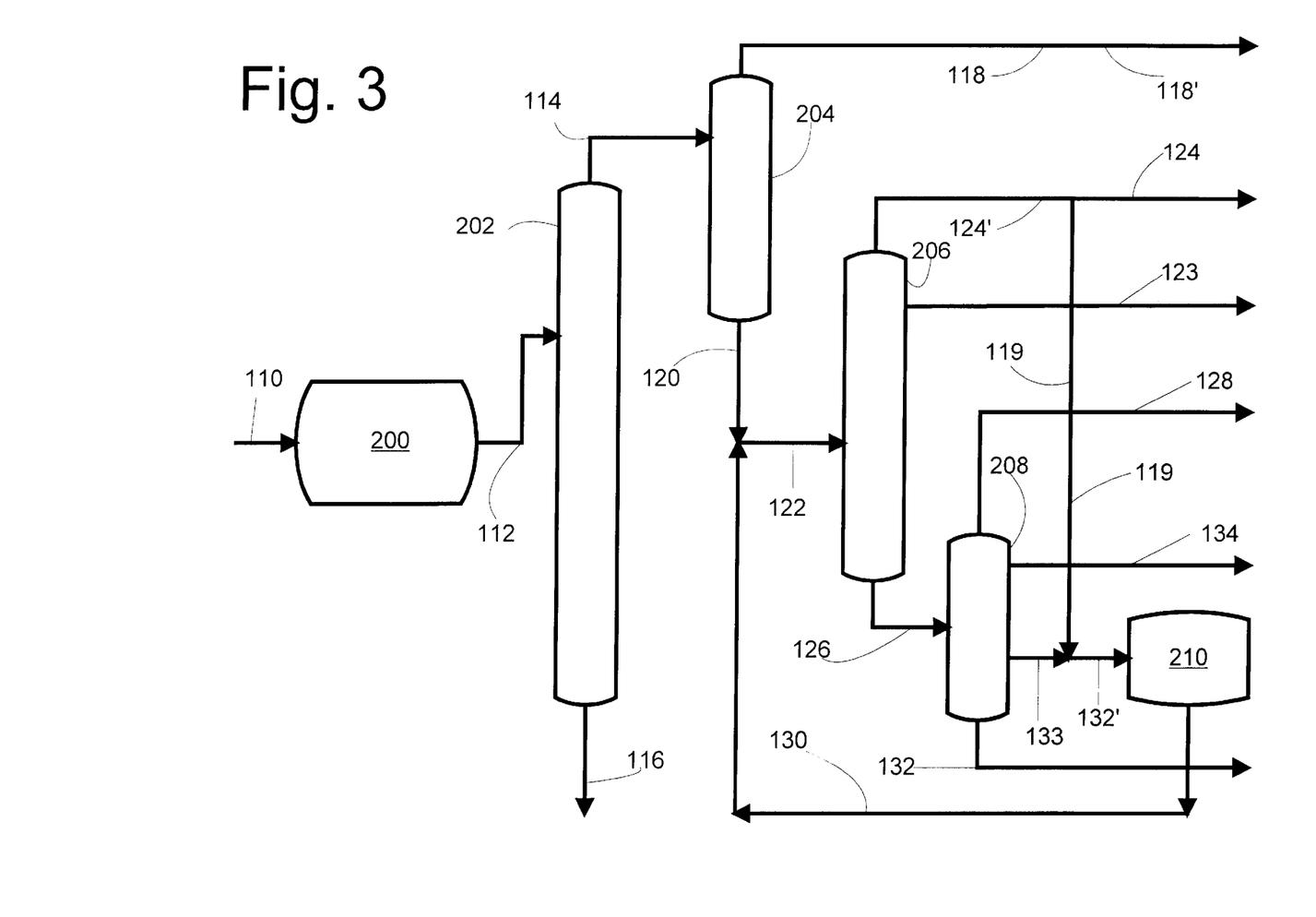
FIG. 3 is a schematic flow sheet representing the process of the invention for the enhancement of an ethylene and propylene yield.

With reference to FIG. 3, an oxygenate feedstream in line 110 is passed to an oxygenate conversion zone 200 to convert at least a portion of the oxygenate feedstream into light olefins as described hereinabove in FIG. 1. A reactor effluent stream comprising light olefins is a withdrawn in line 112 and passed to water separation zone 202. In the water separation zone 202, the reactor effluent stream is flashed at a separation temperature to provide a vapor effluent stream 114 and a water stream 116. As in FIG. 1, the vapor effluent stream 114 may be further conventionally washed with a caustic solution to neutralize acid gases and dried prior to passing the vapor effluent stream 114 to a demethanizer zone 204. In the demethanizer zone 204, conventional distillation occurs to provide a light ends stream (in line 118) and a demethanized stream (in line 120), comprising components heavier than methane. The demethanized stream in line 120 and a metathesized stream in line 130 are passed to a $C_2$ fractionation zone 206 via line 122. An ethylene product stream (in lines 124' and 124) and an ethane product stream (in line 123) are withdrawn from the $C_2$ fractionation zone 206. A $C_3$ plus stream is withdrawn from the bottom of $C_2$ fractionation zone 206 in line 126 and passed to $C_3$ fractionation zone 208. In the $C_3$ fractionation zone 208, the $C_3$ plus stream is fractionated to produce a propylene product stream in line 128, a propane stream in line 134, a butylene stream in line 133 and a heavy ends stream in line 132. The butylene stream in line 133, comprising butylenes, is combined with a portion of the ethylene product stream via lines 124' and 119 and is passed at effective conditions to a metathesis zone 210 via line 132' to produce the metathesized stream in line 130. The metathesized stream in line 130 comprises ethylene, propylene, butylene, and some heavier olefinic components. The ethane, propane, and heavy ends streams in lines 123, 134, and 132 may be used for fuel. The metathesized stream is returned to the $C_2$ fractionation zone via lines 130 and 122 to provide for separation of the additional propylene produced and the return of the unreacted butylene. The heavier olefinic components produced in the metathesis zone are rejected in line 132. Preferably the ratio of ethylene to butylene on a molar basis of ethylene to butylene ranges between about 0.5 to about 5.0.

The following examples are only used to illustrate the present invention and are not meant to be limiting.

EXAMPLES

Example I

Three oxygenate conversion pilot plant runs were conducted using a spray-dried metal alumninophosphate catalyst comprising 40% SAPO-34, 40% kaolin clay and 20% Si—Al binder. The catalyst was loaded into a 2.2 cm (⅞ inch) ID porcelain-lined, stainless steel reactor and placed in a three-zone bronze block furnace. The reactor was heated to 435° C. for Run A. 455° C. for Run B, and 475° C. for Run C under an $N_2$ purge at 138 kPa (5 psig). This condition was held for 1 hour to pretreat the catalyst. The $N_2$ flow was stopped and a methanol/water mixture (80/20 by weight) was introduced at 1 $hr^{-1}$ MeOH WHSV and continued until the reactor effluent contained greater than 50% MeOH and DME. Table 1 summarizes the time on stream and product selectivities at the point where the overall conversion was 99% for each run. It can be seen that increasing reaction temperature increases the ethylene/propylene product ratio, but increasing reaction temperature decreases the catalyst life.

TABLE 1

SUMMARY OF OXYGENATE CONVERSION SELECTIVITIES FOR SAPO-34 WITH INCREASING REACTOR TEMPERATURE

| RUN | A | B | C |
|---|---|---|---|
| Inlet Temp (° C.) | 435 | 455 | 475 |
| Pressure (kPa) | 138 | 138 | 138 |
| MeOH WHSV (hr$^{-1}$) | 1.0 | 1.0 | 1.0 |
| Catalyst Life (hr at >99% Conv) | 4.3 | 3.3 | 2.3 |
| Selectivities at 99% Conversion (mole %) | | | |
| $C_1$ | 3.3 | 4.7 | 7.7 |
| $C_2$ | 0.6 | 0.6 | 0.8 |
| $C_2^=$ | 50.3 | 52.4 | 53.7 |
| $C_3$ | 0.4 | 0.4 | 0.5 |
| $C_3^=$ | 33.5 | 30.8 | 27.0 |
| $C_4 S$ | 9.0 | 7.9 | 6.9 |
| $C_{5+} S$ | 2.0 | 3.1 | 3.2 |
| $C_2^=/C_3^=$ Ratio | 1.50 | 1.70 | 1.99 |

Example II

According to the present invention, the reactor effluent from the oxygenate conversion process of Example I, Run A, at 435° C. is passed to a separation zone consisting of $CO_x$ removal zone and a $H_2O$ separation zone to remove water and provide a hydrocarbon effluent. The hydrocarbon effluent is passed to a demethanizer to remove methane as an overhead stream and provide a demethanizer bottoms stream. The demethanizer bottoms consist of 50.3 equivalents of ethylene, 33.5 equivalents of propylene and 9.0 equivalents of butenes. The demethanizer bottoms stream is combined with a recycle stream from the propylene metathesis reactor consisting of 2.4 equivalents of ethylene, 27.1 equivalents of propylene and 4.0 equivalents of butenes to provide a combined stream to an ethane-ethylene column with 52.7 equivalents of ethylene, 60.6 equivalents propylene and 13.0 equivalents butenes. In the ethane-ethylene column the 52.7 equivalents of ethylene and 0.6 equivalents of ethane are separated overhead and $C_{3+}$ fraction is recovered. The $C_{3+}$ stream is passed to a propane-propylene (P-P) column wherein 13.0 equivalents of butenes and 2.0 equivalents of $C_{5+}$ products are recovered as P-P bottoms. The overhead of the propane-propylene column, consisting of 60.6 equivalents of propylene is divided into two portions; 33.5 equivalents of propylene are passed to a propylene metathesis reactor while 27.1 equivalents of propylene are recovered as a propylene product. The propylene metathesis reactor is operated as described in Example 3 of U.S. Pat. No. 3,723,562 wherein the propylene conversion was 19% with a 37.6% selectivity to ethylene and a 62.4% selectivity to butenes. The entire effluent of this reactor is combined with the demethanizer bottoms as the recycle stream described above.

Thus, in Example II, the addition of a propylene metathesis reactor to convert a portion of the propylene product from the oxygenate conversion zone to ethylene and butene increases the overall ethylene/propylene product ratio from about 1.50 to 1.94. This is accomplished without reducing the catalyst life in the oxygenate conversion process. Comparing the results of Run C in Example I with the improved product ratio of Example II, it can be seen that improved performance can be achieved with a combined oxygenate conversion and $C_3$ metathesis processes without reducing catalyst life.

Example III

According to the present invention, the reactor effluent from the oxygenate conversion process of Example I, Run A, at 435° C. is passed to a separation zone consisting of $CO_x$ removal unit and a $H_2O$ separation to provide a hydrocarbon effluent. The hydrocarbon effluent is passed to a demethanizer to remove methane as an overhead product and a demethanizer bottoms. The demethanizer bottoms consists of 50.3 equivalents ethylene, 33.5 equivalents of propylene and 9.0 equivalents of butenes. The demethanizer bottoms is combined with a recycle stream from the metathesis zone consisting of 12.6 equivalents of ethylene, 142.8 equivalents of propylene and 20.9 equivalents of butenes to provide a combined stream to an ethane-ethylene column containing 62.9 equivalents ethylene, 176.3 equivalents propylene, and 29.9 equivalents butenes. In the ethane-ethylene column, the 62.9 equivalents ethylene and 0.6 equivalents of ethane are separated overhead and a $C_{3+}$ fraction is recovered as ethylene column bottoms which is passed to a propane-propylene (P-P) column. The 29.9 equivalents of butenes and 2.0 equivalents of $C_{5+}$ products are recovered from the bottom of the P-P column. The entire overhead of the propane-propylene column, consisting of 176.3 equivalents or propylene, is passed to the propylene metathesis reactor operating as described in Example 3 of U.S. Pat. No. 3,723,562. The entire effluent of this reactor is combined with bottoms from the demethanizer column as described above. Thus, in Example III, the propylene product of the oxygenate conversion reactor has been essentially completely converted by metathesis to additional ethylene and butenes. This has been accomplished without reducing the catalyst life in the oxygenate conversion process.

Example IV

According to the present invention as illustrated in FIG. 3 hereinabove, the reactor effluent from the oxygenate conversion process of Example I, Run A, at 435° C. is passed to a separation zone consisting of a $H_2O$ separation, $CO_x$ removal unit, and a drier to provide a hydrocarbon effluent. The hydrocarbon effluent is passed to a demethanizer to remove methane as an overhead product and a demethanizer bottoms. The demethanizer bottoms consists of 50.3 equivalents ethylene, 33.5 equivalents of propylene and 9.0 equivalents of butenes. The demethanizer bottoms is combined with a recycle stream from a metathesis zone consisting of 0.5 equivalents of ethylene, 12.0 equivalents of propylene and 9.0 equivalents of butenes to provide a combined stream to recovery in a $C_2$ fractionation column, or an ethane-ethylene column, containing 50.8 equivalents ethylene, 45.5 equivalents propylene, and 18.0 equivalents butenes. In the ethane-ethylene column, the 45.8 equivalents ethylene and the ethane are separated overhead, and a $C_{3+}$ fraction is recovered as ethylene column bottoms which is passed to a propane-propylene (P-P) column where about 45.5 equivalents propylene is recovered as a propylene product. About 18.0 equivalents of butenes are recovered from the bottom of the P-P column. The butenes recovered from the bottom of the P-P column are combined with a portion of the ethylene product to provide a metathesis feed comprising about 5 equivalents of ethylene and about 18 equivalents of butene, representing about a 0.55 molar ratio of ethylene to butene. The metathesis feed is passed to a metathesis reactor operating at about a 50 percent conversion based on moles of butene converted to produce a metathesis reactor effluent comprising about 0.5 equivalents of ethylene, 12.0 equivalents propylene, about 9.0 equivalents butene, and about 2.5 equivalents of heavier olefinic components comprising $C_5$ plus olefinic hydrocarbons. The entire effluent of this reactor is combined with bottoms from the demethanizer column as described above in FIG. 3.

Thus, in Example IV, the butene product of the oxygenate conversion reactor has been essentially completely converted by metathesis to additional ethylene and propylene resulting in about a 50:50 weight distribution of ethylene and propylene products from the complex. This has been accomplished without reducing the catalyst life in the oxygenate conversion process.

We claim:

1. A process for the production of a primary ethylene product stream and a secondary light olefin product stream from an aliphatic hetero compound feedstock, said process comprising the steps of:
   a) reacting said feedstock in the presence of a diluent at effective conditions over a molecular sieve catalyst characterized by an empirical composition on an anhydrous basis by the formula:

$$(EL_xAl_yP_z)O_2$$

where EL is an element selected from the group consisting of silicon, magnesium, zinc, iron, cobalt, nickel, manganese, chromium, and mixtures thereof, x is the mole fraction of EL and is at least 0.005, y is the mole fraction of Al and is at least 0.01, and z is the mole fraction of P and is at least 0.01 and x+y+z=1 to produce a reactor-effluent stream comprising ethylene, propylene, and butylene;
   b) fractionating said reactor effluent stream and a metathesized stream to recover an ethylene stream, a propylene stream, and a butylene stream;
   c) metathesizing at least a portion of a light olefin stream in a metathesis zone at effective conditions, said light olefin stream selected from the group consisting of the ethylene stream, the propylene stream, the butylene stream, and mixtures thereof, to produce said metathesized stream comprising ethylene, propylene, and butylene; and,
   d) returning said metathesized stream to said fractionating step, and withdrawing the ethylene stream as the primary ethylene product stream and a secondary light olefin product stream selected from the group consisting of the propylene stream, the butylene stream and mixtures thereof.

2. The process of claim 1 wherein the light olefin stream undergoing metathesis in the metathesis zone consists of the ethylene stream and the butylene stream to produce the metathesized stream comprising propylene and recovering the propylene stream in step (b) as the secondary light olefin product stream.

3. The process of claim 2 wherein the ethylene stream and the butylene stream undergoing metathesis in the metathesis zone are introduced to the metathesis zone in a molar ratio of ethylene to butylene ranging between the 0.5 and about 5.0.

4. The process of claim 1 wherein the light olefin stream undergoing metathesis in the metathesis zone consists of the propylene stream, to produce the metathesized stream comprising ethylene and butylene and recovering the butylene stream in step (b) as the secondary light olefin product stream.

5. The process of claim 4 wherein a ratio of the ethylene product to the secondary light olefin product stream ranges from about 0.1 to about 1000.

6. The process of claim 1 wherein the molecular sieve catalyst is selected from the group consisting of SAPO-34, SAPO-17, and mixtures thereof.

7. The process of claim 1 wherein the aliphatic hetero compound feedstock is selected from the group consisting of methanol, ethanol, dimethyl ether, and mixtures thereof.

8. A process for the production of a primary ethylene product stream and a secondary light olefin product stream comprising propylene from a feedstock comprising methanol or dimethyl ether, said process comprising the steps of:
   a) reacting said feedstock in the presence of a diluent at effective conditions over a SAPO catalyst selected from the group consisting of SAPO-34, SAPO-17 and mixtures thereof to produce a reactor effluent stream comprising ethylene, propylene, and butylene;
   b) fractionating said reactor effluent stream and a metathesized stream to recover an ethylene stream, a propylene stream, and a butylene stream;
   c) metathesizing at least a portion of the ethylene stream and a portion of the butylene stream in a metathesis zone at effective conditions, said to produce said metathesized stream comprising ethylene, propylene, and butylene; and,
   d) returning said metathesized stream to said fractionating step, and withdrawing the ethylene stream as the primary ethylene product stream and the propylene stream as the secondary light olefin product stream.

9. The process of claim 8 wherein the ethylene stream and the butylene stream undergoing metathesis in the metathesis zone are introduced to the metathesis zone in a molar ratio of ethylene to butylene ranging between about 0.5 and about 5.0.

10. The process of claim 8 wherein the metathesized stream consists essentially of propylene and unreacted butylene.

11. A process for the production of a primary ethylene product stream and a secondary light olefin product stream comprising butylene from a feedstock comprising methanol or dimethyl ether, said process comprising the steps of:
   a) reacting said feedstock in the presence of a diluent at effective conditions over a SAPO catalyst selected from the group consisting of SAPO-34, SAPO-17 and mixtures thereof to produce a reactor effluent stream comprising ethylene, propylene, and butylene;
   b) fractionating said reactor effluent stream and a metathesized stream to recover an ethylene stream, a propylene stream, and a butylene stream;
   c) metathesizing at least a portion of the propylene stream in a metathesis zone at effective conditions, said to produce said metathesized stream comprising ethylene, and butylene; and,
   d) returning said metathesized stream to said fractionating step, and withdrawing the ethylene stream as the primary ethylene product stream and the butylene stream as the secondary light olefin product stream.

12. The process of claim 11 wherein the metathesized stream consists essentially of ethylene and butylene.

13. The process of claim 11 wherein a ratio of said primary ethylene product stream to the secondary light olefin product stream, comprising butylene ranges from about 0.5 to about 2.

14. The process of claim 11 further comprising isomerizing a portion of said secondary light olefin product stream comprising 1-butene and 2-butene to form 1-butene and recovering a 1-butene product.

15. The process of claim 14 wherein said isomerization of said butylene stream comprises passing said portion of said butylene stream to a catalytic distillation zone containing a non-zeolitic molecular sieve catalyst selected from the group consisting of SAPO-11, SAPO-31, SAPO-41 and mixtures thereof.

16. The process of claim 15 wherein said catalytic distillation zone is operated at conditions including a temperature from about 50° C. to about 300° C. and pressure from about 100 kPa to about 7 MPa.

* * * * *